(12) United States Patent
Cho et al.

(10) Patent No.: US 9,326,694 B2
(45) Date of Patent: May 3, 2016

(54) MOBILE TERMINAL FOR MEASURING BIOLOGICAL SIGNAL

(75) Inventors: Jae Geol Cho, Yongin-si (KR); Sang Hun Lee, Yongin-si (KR); Chul Ho Cho, Seongnam-si (KR); Sun Tae Jung, Yongin-si (KR)

(73) Assignee: Samsung Electronics Co., Ltd., Yeongtong-gu, Suwon-si, Gyeonggi-do (KR)

( * ) Notice: Subject to any disclaimer, the term of this patent is extended or adjusted under 35 U.S.C. 154(b) by 1036 days.

(21) Appl. No.: 12/350,282

(22) Filed: Jan. 8, 2009

(65) Prior Publication Data

US 2009/0182205 A1    Jul. 16, 2009

(30) Foreign Application Priority Data

Jan. 10, 2008  (KR) .................. 10-2008-0002933

(51) Int. Cl.
*A61B 5/00*      (2006.01)
*G06F 19/00*     (2011.01)
(Continued)

(52) U.S. Cl.
CPC .............. *A61B 5/0404* (2013.01); *A61B 5/0261* (2013.01); *G06F 19/3418* (2013.01); *A61B 5/0006* (2013.01); *A61B 5/02416* (2013.01); *A61B 5/02438* (2013.01); *A61B 5/6898* (2013.01); *A61B 2560/0468* (2013.01)

(58) Field of Classification Search
CPC .............. A61B 5/0452; A61B 5/0404; A61B 5/02438; A61B 5/0002; A61B 5/0261; G06F 19/3418; G06F 19/3406

USPC ......... 600/300–301, 309, 363–365, 372–374, 600/377–379, 382–384, 386–397, 446, 465, 600/481, 485, 500–503, 508–509, 600/515–519; 128/920–925; 705/2–3
See application file for complete search history.

(56) References Cited

U.S. PATENT DOCUMENTS 3,848,582 A * 11/1974 Milani et al. .................. 600/372
4,535,783 A *  8/1985 Marangoni .................... 600/524
(Continued)

FOREIGN PATENT DOCUMENTS

JP        2005-46215 A      2/2005
KR   10-2006-0116190 A     11/2006
KR   10-2007-0011685 A      1/2007

OTHER PUBLICATIONS

NPL_OMRON_2006.pdf, pp. 1-128.*

*Primary Examiner* — William Thomson
*Assistant Examiner* — Marie Archer
(74) *Attorney, Agent, or Firm* — Cha & Reiter, LLC.

(57) ABSTRACT

A mobile terminal for measuring a biological signal is disclosed. The mobile terminal for measuring a biological signal includes an electrocardiogram electrode unit having a first electrode provided in a front surface of a body of the mobile terminal and a second electrode provided in a first side surface of the mobile terminal body for measuring an electrocardiogram signal through the first electrode and the second electrode, a sensor unit provided in a second side surface of the mobile terminal body for measuring a pulse wave signal, a controller provided within the mobile terminal for analyzing the electrocardiogram signal received from the electrocardiogram electrode unit and the pulse wave signal received from the sensor unit and a radio frequency unit for transmitting an analyzed result by the control of the controller.

7 Claims, 4 Drawing Sheets

(51) Int. Cl.
  *A61B 5/0404* (2006.01)
  *A61B 5/026* (2006.01)
  *A61B 5/024* (2006.01)

(56) References Cited

U.S. PATENT DOCUMENTS

| | | | | |
|---|---|---|---|---|
| 4,606,352 | A * | 8/1986 | Geddes et al. | 600/515 |
| 4,825,874 | A * | 5/1989 | Uhlemann | 600/523 |
| 5,191,891 | A * | 3/1993 | Righter | 600/523 |
| 5,365,935 | A * | 11/1994 | Righter et al. | 600/523 |
| 5,623,926 | A * | 4/1997 | Weiss | 600/509 |
| 7,471,976 | B2 * | 12/2008 | Lin et al. | 600/509 |
| 2002/0095093 | A1 * | 7/2002 | Au et al. | 600/509 |
| 2002/0143576 | A1 * | 10/2002 | Nolvak et al. | 705/2 |
| 2004/0193063 | A1 * | 9/2004 | Kimura et al. | 600/500 |
| 2005/0004487 | A1 * | 1/2005 | Ishida et al. | 600/523 |
| 2005/0027203 | A1 * | 2/2005 | Umeda et al. | 600/509 |
| 2005/0143666 | A1 * | 6/2005 | Yanaga | 600/509 |
| 2005/0143670 | A1 * | 6/2005 | Umeda et al. | 600/509 |
| 2006/0047214 | A1 * | 3/2006 | Fraden | 600/513 |
| 2006/0200011 | A1 * | 9/2006 | Suzuki et al. | 600/301 |
| 2006/0217620 | A1 * | 9/2006 | Bojovic et al. | 600/509 |
| 2006/0224073 | A1 * | 10/2006 | Lin et al. | 600/513 |
| 2007/0021676 | A1 * | 1/2007 | Han et al. | 600/509 |
| 2007/0021677 | A1 * | 1/2007 | Markel | 600/509 |
| 2007/0129220 | A1 * | 6/2007 | Bardha | 482/82 |
| 2007/0173726 | A1 * | 7/2007 | Kim et al. | 600/483 |
| 2007/0255122 | A1 * | 11/2007 | Vol et al. | 600/301 |
| 2007/0299322 | A1 * | 12/2007 | Miyajima et al. | 600/301 |
| 2008/0108890 | A1 * | 5/2008 | Teng et al. | 600/372 |
| 2009/0062670 | A1 * | 3/2009 | Sterling et al. | 600/509 |
| 2009/0070266 | A1 * | 3/2009 | Shah et al. | 705/51 |

* cited by examiner

MOBILE TERMINAL FOR MEASURING BIOLOGICAL SIGNAL

CLAIM OF PRIORITY

This application claims the benefit of the earlier filing date, pursuant to 35 USC 119, to that patent application entitled "MOBILE TERMINAL FOR MEASURING BIOLOGICAL SIGNAL" filed in the Korean Intellectual Property Office on Jan. 10, 2008 and assigned Serial No. 10-2008-0002933, the contents of which are incorporated herein by reference.

BACKGROUND OF THE INVENTION

1. Field of the Invention

The present invention relates to a biological signal measurement, and more particularly, to a mobile terminal for measuring a biological signal that can be carried by a user.

2. Description of the Related Art

A ubiquitous environment relates to a technology whereby various information can be transmitted and received by freely connecting to a network almost regardless of time and location, with which many users can share various information.

Particularly, healthcare can be provided in a ubiquitous environment (U-healthcare), whereby a user can receive a medical treatment service through a network without visiting a medical facility and the user's health state can be inspected at any time. Various appliances have now been developed for the provision of U-healthcare.

In general, a user measures electrocardiogram signals and a pulse wave of the heart using medical measurement instruments having a patch type electrocardiogram electrode and a clip type optical sensor. Because such medical measurement instruments have several connection leads for connecting electrocardiogram electrodes and optical sensors and have a large bulk, generally the user cannot perform an electrocardiogram inspection while carrying the instruments.

SUMMARY OF THE INVENTION

The present invention provides a mobile terminal that can measure an electrocardiogram signal and a pulse wave and that can be carried by a user.

In accordance with an aspect of the present invention, a mobile terminal for measuring a biological signal includes an electrocardiogram electrode unit having a first electrode provided in a front surface of a body of the mobile terminal and a second electrode provided in a first side surface of the mobile terminal body for measuring an electrocardiogram signal through the first electrode and the second electrode, a sensor unit provided in a second side surface of the mobile terminal body for measuring a pulse wave signal, a controller provided within the mobile terminal for analyzing the electrocardiogram signal received from the electrocardiogram electrode unit and the pulse wave signal received from the sensor unit and a radio frequency (RF) unit for transmitting an analyzed result by the control of the controller.

BRIEF DESCRIPTION OF THE DRAWINGS

The above features and advantages of the present invention will be more apparent from the following detailed description in conjunction with the accompanying drawings, in which.

DETAILED DESCRIPTION OF THE INVENTION

Exemplary embodiments of the present invention are described in detail with reference to the accompanying drawings. The same reference numbers are used throughout the drawings to refer to the same or like parts. The views in the drawings are schematic views only, and are not intended to be to scale or correctly proportioned. Detailed descriptions of well-known functions and structures incorporated herein may be omitted to avoid obscuring the subject matter of the present invention.

In the following description, a 'mobile terminal' can transmit and receive data to and from various terminals and includes almost all types of portable terminals that can be carried in the hand of a user. The mobile terminal includes, for example, a cellular phone, Moving Picture Experts Group layer-3 (mp3) player, and portable medical measurement terminal. Further, the mobile terminal may include accessories for use by attaching to the cellular phone or the terminal.

A 'terminal' includes information processing appliances and/or applications for transmitting and receiving data and for processing the transmitted and received data. The terminal includes at least one of a mobile terminal, a computer, and medical appliances.

Figure 1:
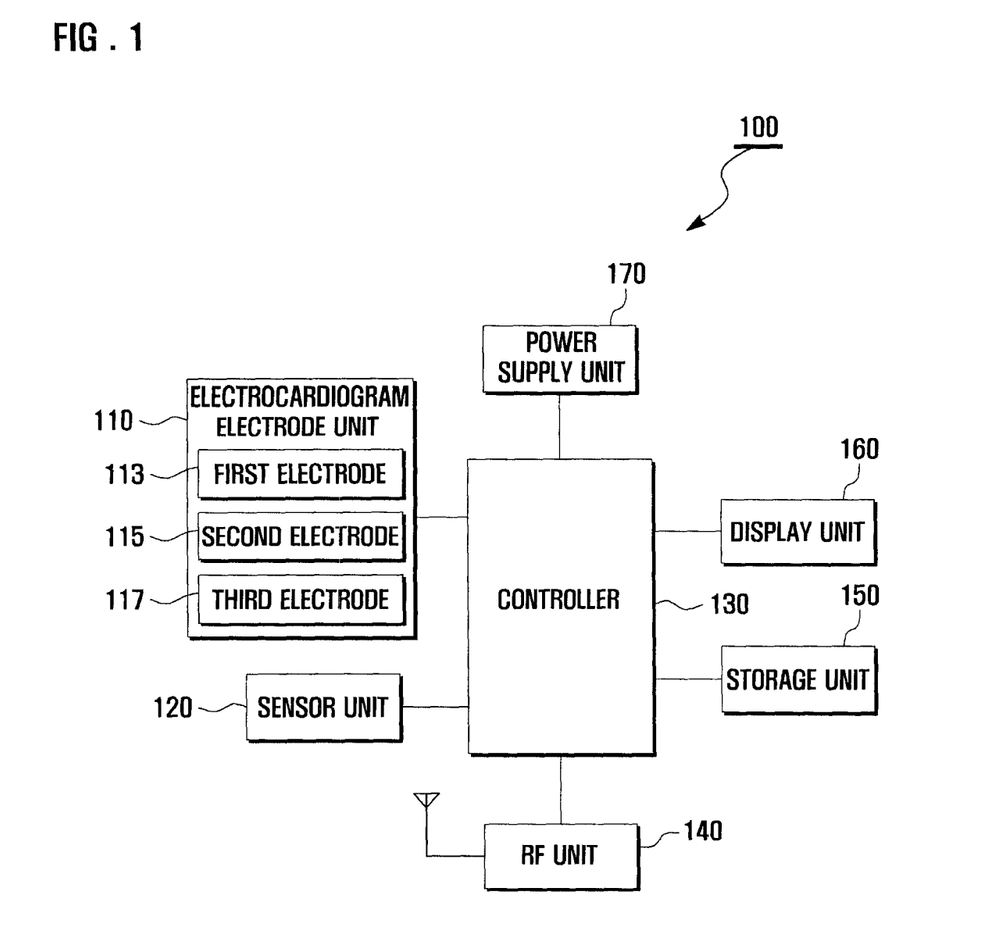
FIG. 1 is a block diagram illustrating a configuration of a mobile terminal for measuring a biological signal according to an exemplary embodiment of the present invention.

FIG. 1 is a block diagram illustrating a configuration of a mobile terminal for measuring a biological signal according to an exemplary embodiment of the present invention.

Referring to FIG. 1, a mobile terminal 100 includes an electrocardiogram electrode unit 110, sensor unit 120, controller 130, RF unit 140, storage unit 150, display unit 160, power supply unit 170, and terminal body (not shown in FIG. 1).

The electrocardiogram electrode unit 110 includes a first electrode 113 and a second electrode 115 having different polarity and measures a biological electrocardiogram signal when in contact with a part of a user's body. The electrocardiogram electrode unit 110 further includes a third electrode 117. An error of an electrocardiogram signal measured through the first electrode 113 and the second electrode 115 may be reduced by using the third electrode 117. In the exemplary embodiment, the first electrode 113 is an electrode having positive (+) polarity, the second electrode 115 is an electrode having negative (−) polarity, and the third electrode 117 is an electrode having a ground polarity. The electrocardiogram electrode unit 110 measures an electrocardiogram signal by a sequential change of a myocardium cellular operation potential that is generated according to the user's heartbeat using a potential difference of the first electrode 113 and the second electrode 115 relative to the third electrode 117. The electrocardiogram electrode unit 110 is mounted in the terminal body of the mobile terminal 100 to contact a part of the user's body. Upon contacting a part of the user's body, the contact with a part of the user's body is detected and the electrocardiogram electrode unit 110 measures an electrocardiogram signal and outputs the measured electrocardiogram signal to the controller 130. One of the electrodes 113, 115, and 117, included in the electrocardiogram electrode unit 110, may further be set as a switch, so that when the electrode that is set as a switch is triggered, the electrocardiogram electrode unit 110 measures an electrocardiogram signal and outputs the measured electrocardiogram signal to the controller 130.

The sensor unit 120 includes an optical sensor, e.g. a reflective optical sensor. The sensor unit 120 measures a biological pulse wave signal when contacting a part of the user's body and outputs the measured pulse wave signal to the controller 130. Particularly, the reflective optical sensor includes a light-emitting diode (LED) for emitting light and a photo diode for determining a scattered light amount. When the user contacts a part of their body (for example, a finger) with the reflective optical sensor, the LED of the reflective optical sensor emits light to the contacted part of the user's body. The photodiode of the reflective optical sensor measures the amount of light reflected from the contacted part of the user's body and the reflective optical sensor outputs the measured light amount to the controller 130. The light amount measured by the photo diode changes according to a quantity of red blood corpuscles flowing within the body. The amount of light measured depends on a change of blood flow caused by the user's heartbeat. A pulse wave can be measured from the change of the measured light amount.

In the exemplary embodiment, the sensor unit 120 is a reflective optical sensor. However the sensor unit 120 may be a more complex sensor that can measure a pulse, subcutaneous fat thickness, body fat rate, skin color, and pulse wave signal of the user. The sensor unit 120 may be mounted at the outside of the mobile terminal 100 in order to contact a part of the user's body.

The controller 130 is provided within the mobile terminal 100 and controls general operations and states of constituent units provided in the mobile terminal 100. Particularly, when power is supplied through the power supply unit 170, the controller 130 determines whether a contact is detected in the electrocardiogram electrode unit 110 and the sensor unit 120, or whether an electrode, that is set as a switch, is triggered. If a contact is detected, or if an electrode that is set as a switch is triggered, the controller 130 analyzes an electrocardiogram signal received through the electrocardiogram electrode unit 110 and a pulse wave signal received through the sensor unit 120 to determine a pulse wave transmission time period. The pulse wave transmission time period is a time period in which a pulsation pressure wave is transmitted from a main artery valve to a peripheral portion, and is used to determine a vein elasticity degree. Specifically, a vein elasticity degree can be determined from a pulse wave transmitting velocity calculated by dividing a vein length by the measured pulse wave transmission time period. The vein length is obtained either by the user measuring a distance from a neck to a fingertip and directly inputting the distance to the mobile terminal 100, or is obtained through the user's body information (for example, a height and sex distinction) that may be downloaded from another terminal and input to the mobile terminal 100.

The RF unit 140 performs a communication function with other terminals. The RF unit 140 may perform short range communication using means such as Bluetooth and a wireless communication function using means such as wireless local area network (WLAN). Accordingly, the RF unit 140 transmits the pulse wave transmission time period determined by the controller 130 and transmits data corresponding to a vein elasticity degree determined using the pulse wave transmission time period to another terminal (not shown).

The storage unit 150 stores application programs necessary for operation of the mobile terminal 100, and stores data generated according to operation of the mobile terminal 100 and data received from the controller or via the RF unit 140. Particularly, the storage unit 150 stores an electrocardiogram signal and a pulse wave signal measured through the electrocardiogram electrode unit 110 and the sensor unit 120, respectively, under the control of the controller 130 and stores the pulse wave transmission time period determined by analyzing the measured electrocardiogram signal and pulse wave signal.

The display unit 160 displays information related to a state and operation of the mobile terminal 100. For example, the display unit 160 may display an electrocardiogram signal and a pulse wave signal, measured under the control of the controller 130, with a graph and may display a pulse wave transmission time period determined through the electrocardiogram signal and the pulse wave signal.

The power supply unit 170 controls power supplied of the mobile terminal 100. The power supply unit 170 includes a button, and when the button is pressed by the user, the controller 130 detects the action and controls the power supply unit 170 to supply power to units of the mobile terminal 100.

When power is supplied through the power supply unit 170, the controller 130 controls the electrocardiogram electrode unit 110 and the sensor unit 120 to measure an electrocardiogram signal and a pulse wave signal, respectively. The controller 130 determines a pulse wave transmission time period through the measured electrocardiogram signal and pulse wave signal and determines a vein elasticity degree through the determined pulse wave transmission time period. The controller 130 may transmit the determined pulse wave transmission time period and vein elasticity degree to another terminal (not shown) through the RF unit 140, or control the display unit 160 to display the pulse wave transmission time period and vein elasticity degree. Further, the controller 130 may control the storage unit 150 to store the measured electrocardiogram signal and pulse wave signal, and the determined pulse wave transmission time period. Although the invention is described with regard to providing a vein elasticity degree, it would be recognized other similar body characteristics associated with blood measurement may be determined and provided to a display or another terminal.

Figure 2:
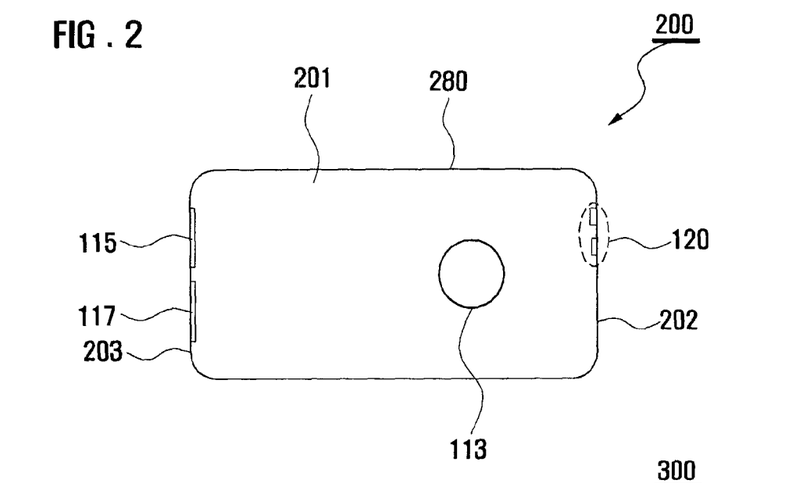
FIG. 2 is a plan view illustrating a mobile terminal for measuring a biological signal having one sensor unit and three electrocardiogram electrodes according to another exemplary embodiment of the present invention.

FIG. 2 is a plan view illustrating a mobile terminal for measuring a biological signal having one sensor unit and three electrocardiogram electrodes according to another exemplary embodiment of the present invention.

As shown in FIG. 2, a mobile terminal 200 for measuring a biological signal has the sensor unit 120 at an upper end of a right side surface 202 of a terminal body 280. The sensor unit 120 uses an optical sensor, and the optical sensor includes a Light Emitting Diode (LED) for emitting light and a photo diode (PD) for measuring an amount of light reflected from the body.

The first electrode 113 of the electrocardiogram electrode unit 110 is provided on a front surface 201 of the terminal body 280, and the second electrode 115 and third electrode 117 of the electrocardiogram electrode unit 110 are provided at a side surface of the terminal body 280. In this illustrated case, a left side surface 203. The first electrode 113 is set as a switch, and when the first electrode 113 is triggered, the controller 130 determines this as a start instruction for measuring a biological signal.

Accordingly, when the user intends to measure a biological signal of a hand and arm using the mobile terminal 200, the user contacts a finger with the optical sensor of the sensor unit 120 and contacts another finger of the same hand with the first electrode 113. The user contacts the left side surface 203 at which the second electrode 115 and the third electrode 117 are provided with the arm of the hand opposite to that contacting the sensor unit 120 and then triggers the first electrode 113. The controller 130 detects the triggering action and determines a pulse wave transmission time period using an electrocardiogram signal and a pulse wave signal measured through the electrocardiogram electrode unit 110 and the sensor unit 120, respectively. The controller 130 determines a vein elasticity degree using the determined pulse wave transmission time period. Thereafter, the controller 130 transmits the determined vein elasticity degree to another terminal through the RF unit 140 and controls the storage unit 150 to store the measured pulse wave signal and electrocardiogram signal, pulse wave transmission time period, and vein elasticity degree.

In the mobile terminal 200 according to the present exemplary embodiment, the sensor unit 120 is provided in the right side surface 202, and the first electrode is set as a switch to measure a biological signal. However, it would be recognized that however the sensor unit 120 may be provided in the left side surface 203, and the second electrode 115 and the third electrode 117 may be provided in the right side surface 202. Further, although not shown in FIG. 2, the power supply unit 170 may be provided adjacent to the sensor unit 120, and the display unit 160 may be provided adjacent to the first electrode 113.

The controller 130 may control the display unit 160 to display the measured electrocardiogram signal, pulse wave signal, and pulse wave transmission time period. Further, the mobile terminal 200 having the configuration of FIG. 2 can determined a pulse wave transmission time period of an arm contacting the optical sensor of the sensor unit 120.

FIGS. 3A to 5 illustrate configurations of a mobile terminal that can determine a pulse wave transmission time period of both arms simultaneously.

Figure 3A:
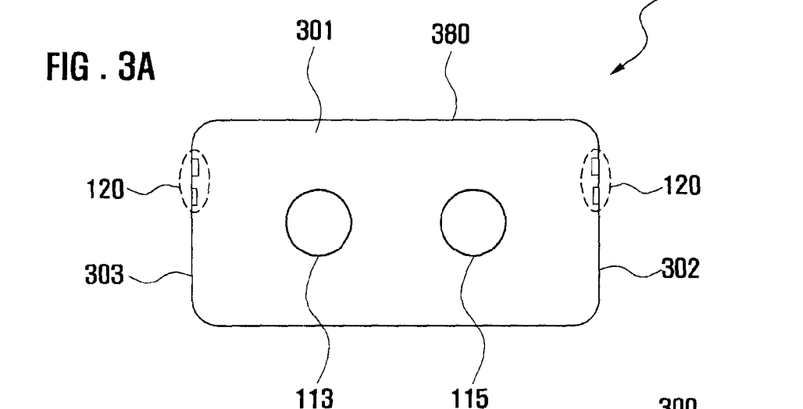
FIGS. 3A and 3B are plan views illustrating a mobile terminal for measuring a biological signal having two sensor units and three electrocardiogram electrodes according to another exemplary embodiment of the present invention.
Figure 3B:
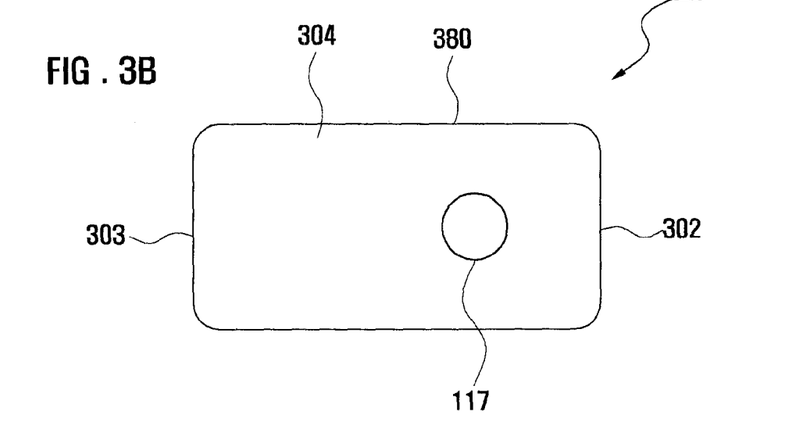

FIGS. 3A and 3B are plan views illustrating a mobile terminal for measuring a biological signal having two sensor units and three electrocardiogram electrodes according to another exemplary embodiment of the present invention.

Referring to FIG. 3A, a mobile terminal 300 has two sensor units 120 provided at an upper end of the right and left side surfaces 302 and 303 of the terminal body 380 and has first electrode 113 and second electrode 115 provided at the front surface 301 of the terminal body 380.

As shown in FIG. 3B, the mobile terminal 300 has third electrode 117 provided at a rear side 304 of the terminal body 380, at a position of the rear side 304 corresponding to the position of second electrode 115 on the front surface 301 of the terminal body 380. Although not shown in FIGS. 3A and 3B, the mobile terminal 300 may further include the power supply unit 170 and the display unit 160. Accordingly, power is supplied to the mobile terminal through the power supply unit 170 and the user contacts a finger of one hand with one of the sensor units 120 and a finger of the other hand with the other sensor unit 120. The user then contacts another finger of one hand with the first electrode 113 and another finger of the other hand contacts the second electrode 115 of the first surface 301 of the terminal body 380, and contacts a third finger of the hand contacting the second electrode 115 to the third electrode 117.

The controller 130 determines a pulse wave transmission time period by analyzing an electrocardiogram signal and a pulse wave signal measured through the electrocardiogram electrode unit 10 and the sensor unit 120, respectively. The controller 130 then determines a vein elasticity degree using the determined pulse wave transmission time period. Thereafter, the controller 130 transmits the determined vein elasticity degree to another terminal through the RF unit 140 and controls the storage unit 150 to store the measured pulse wave signal and electrocardiogram signal, pulse wave transmission time period, and vein elasticity degree.

Figure 4:
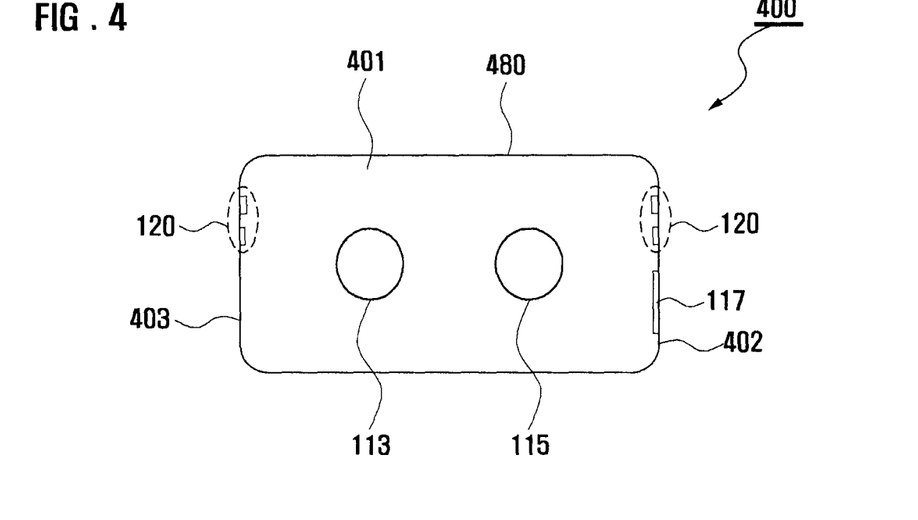
FIG. 4 is a plan view illustrating a mobile terminal for measuring a biological signal having two sensor units and three electrocardiogram electrodes according to another exemplary embodiment of the present invention.

FIG. 4 is a plan view illustrating a mobile terminal for measuring a biological signal having two sensor units and three electrocardiogram electrodes according to another exemplary embodiment of the present invention.

Referring to FIG. 4, a mobile terminal 400 has two sensor units 120 provided at an upper end of the right side surface 402 and the left side surface 403 of the terminal body 480 and has the first electrode 113 and the second electrode 115 provided at the front surface 401 of the terminal body 480. Further, the mobile terminal 400 has the third electrode 117 provided at a lower end of either the right side surface 402 or the left side surface 403 at which the sensor unit 120 is provided. Preferably, the third electrode 117 is positioned at the side surface nearest to the second electrode 115. The controller 130 determines a pulse wave transmission time period by analyzing an electrocardiogram signal and a pulse wave signal measured through the electrocardiogram electrode unit 110 and the sensor unit 120, respectively. Further, the controller 130 transmits the determined pulse wave transmission time period through the RF unit 140 to another terminal. Although not shown in FIG. 4, the mobile terminal 400 may further include the power supply unit 170 and the display unit 160.

Figure 5:
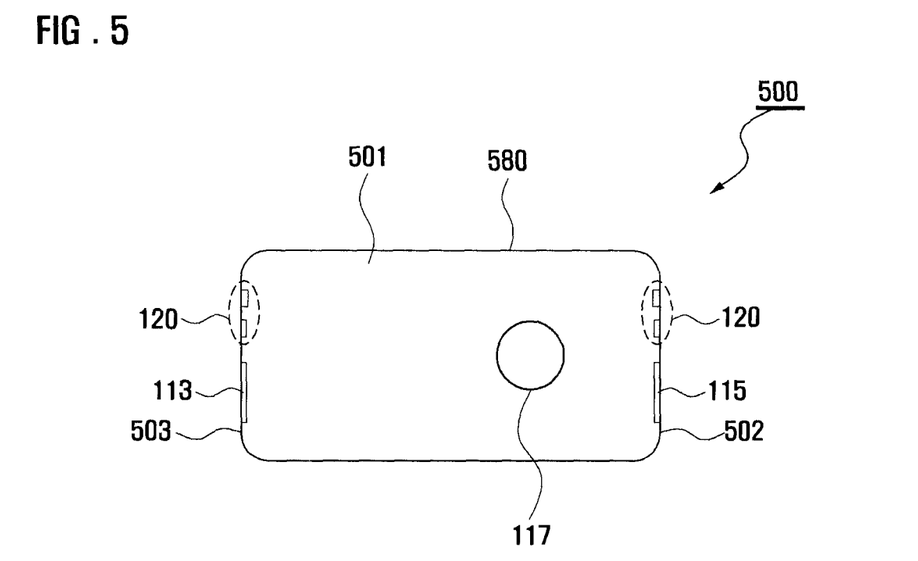
FIG. 5 is a plan view illustrating a mobile terminal for measuring a biological signal having two sensor units and three electrocardiogram electrodes according to another exemplary embodiment of the present invention.

FIG. 5 is a plan view illustrating a mobile terminal for measuring a biological signal having two sensor units and three electrocardiogram electrodes according to another exemplary embodiment of the present invention.

Referring to FIG. 5, a mobile terminal 500 has two sensor units 120 provided at an upper end of the right side surface 502 and the left side surface 503 of the terminal body 580 and has a first electrode 113 and a second electrode 115 at a lower end of the left side surfaces 503 and the right side surface 502, respectively, at which the sensor units 120 are provided. The third electrode 117 is provided at the front surface 501 of the terminal body 580. In this case, the user contacts a finger of one hand with the left side surface 503 and a finger of the other hand with the right side surface 502 of the mobile terminal 500, and contacts another finger of either hand with the third electrode 117. Accordingly, the controller 130 determines a pulse wave transmission time period through an electrocardiogram signal and a pulse wave signal measured through the electrocardiogram electrode unit 110 and the sensor unit 120, respectively. The controller 130 determines a vein elasticity degree using the determined pulse wave transmission time period. Thereafter, the controller 130 transmits the determined vein elasticity degree to another terminal through the RF unit 140 and controls the storage unit 150 to store the measured pulse wave signal and electrocardiogram signal, pulse wave transmission time period, and vein elasticity degree. Although not shown in FIG. 5, the mobile terminal 500 may further include the power supply unit 170 and the display unit 160.

The mobile terminal of the above-described exemplary embodiments measures a biological signal with a method similar to that of medical measurement instruments.

Figure 6:
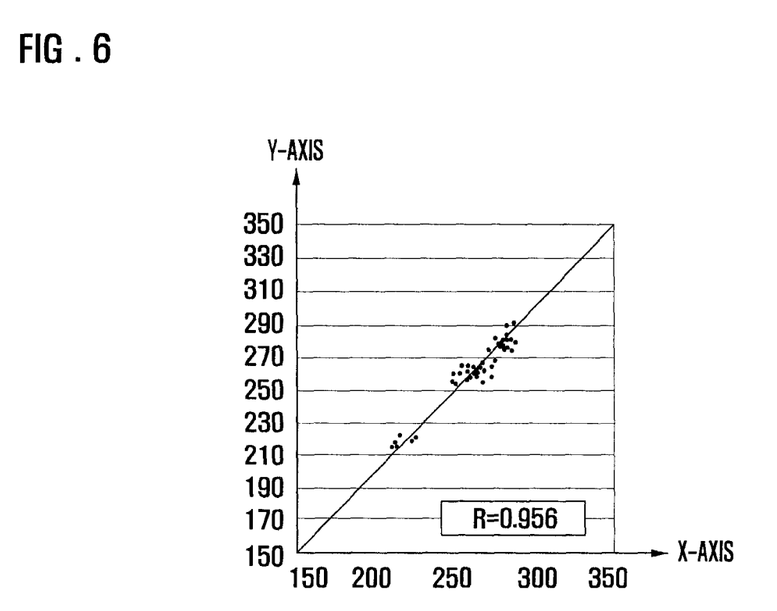
FIG. 6 is a graph illustrating measurement results measured in a mobile terminal and a medical measurement instrument according to another exemplary embodiment of the present invention.

FIG. 6 is a graph comparing a biological signal measured using a mobile terminal described herein and that measured using a medical measurement instrument in the same condition.

In FIG. 6, the X-axis represents a vein elasticity degree determined using the medical measurement instrument and the Y-axis represents a vein elasticity degree determined using the mobile terminal according to the present invention. A correlation coefficient R represents a degree to which a vein elasticity degree determined using the mobile terminal correlates with that determined using a medical measurement instrument, wherein when a value of the X-axis equates to a value of the Y-axis, the correlation coefficient R is equal to 1.

Referring to FIG. 6, a correlation coefficient R between a biological signal determined using the mobile terminal according to the present invention and a biological signal determined using the medical measurement instrument in the same condition is equal to 0.956.

In the foregoing descriptions of exemplary embodiments of the mobile terminal according to the present invention, a position at which the electrocardiogram electrode unit 110 and the sensor unit 120 are provided is described. However, the positions at which the electrocardiogram electrode unit 110 and the sensor unit 120 are provided are not limited thereto, and the electrocardiogram electrode unit 110 and the sensor unit 120 may be provided at various positions of the mobile terminal. For example, in the mobile terminal, the display unit 160 may be provided in the front surface of the terminal body, the sensor unit 120 may be provided at an upper edge of the terminal body, or the sensor unit 120 may be provided at a lower edge thereof. Further, in the exemplary embodiments of the present invention, the mobile terminal has a quadrangular shape, however the present invention is not limited thereto and may be formed in various shapes such as an oval shape.

As described above, according to the present invention, a user can inspect an electrocardiogram and pulse wave without visiting a medical facility using a mobile terminal having two or more electrodes and at least one optical sensor. Because information about the electrocardiogram and pulse wave inspected through the mobile terminal can be transmitted to another terminal using a wireless transmission, a vein health condition value can be measured and analyzed by health care personnel without requiring the user to visit a medical facility.

The above-described methods according to the present invention can be realized in hardware or as software or computer code that can be stored in a recording medium such as a CD ROM, an RAM, a floppy disk, a hard disk, or a magneto-optical disk or downloaded over a network, so that the methods described herein can be executed by such software using a general purpose computer, or a special processor or in programmable or dedicated hardware, such as an ASIC or FPGA. As would be understood in the art, the computer, the processor or the programmable hardware include memory components, e.g., RAM, ROM, Flash, etc. that may store or receive software or computer code that when accessed and executed by the computer, processor or hardware implement the processing methods described herein.

Although the invention has been described with regard to the electrodes and/or sensors being placed "in" the mobile terminal, it would be recognized that the access points to the electrodes and/or sensors are placed "on" the mobile terminal. It would be understood that when referring to the electrodes and/or sensors, reference is also made to the ability to access the corresponding electrodes and/or sensors. Hence, while the sensors may be placed in the mobile device, the access to the sensors may be placed on the mobile device. Similarly, the electrodes and/or sensors may be surface mounted onto the mobile device. In additions combinations of placement of electrodes and/or sensor "in" and "on" the mobile device are considered within the scope of the invention. Hence, the terms "in" and "on" with regard to the electrodes and/or sensors are used interchangeably herein.

Although exemplary embodiments of the present invention have been described in detail hereinabove, it should be clearly understood that many variations and modifications of the basic inventive concepts herein described, which may appear to those skilled in the art, will still fall within the spirit and scope of the exemplary embodiments of the present invention as defined in the appended claims.

What is claimed is:

1. A mobile terminal for measuring biological signals, comprising:
    an electrocardiogram electrode unit having a first electrode provided on a front surface of a body of the mobile terminal to enable contact with a first finger of a hand, and a second electrode and a third electrode each provided on a first side surface of the mobile terminal body to enable contact with an arm opposite to the hand and for measuring an electrocardiogram signal as a first biological signal through the first electrode, the second electrode, and the third electrode, wherein the second and third electrodes are positioned at the first side surface of the mobile terminal body;
    a reflective optical sensor unit having a light source for emitting light at tissue, and having a light receiver for receiving the emitted light reflected by the tissue, with the reflective optical sensor unit positioned at a second side surface on an opposite side of the mobile terminal body from the first side surface at which the second and third electrodes are positioned to enable contact with a second finger of the hand simultaneously with contact of the first electrode with the first finger and for optically measuring a pulse wave signal of the tissue from the received reflected light, and for generating a second biological signal from the pulse wave signal;
    a controller provided within the mobile terminal for analyzing the electrocardiogram signal received from the electrocardiogram electrode unit and the second biological signal received from the optical sensor unit to determine a pulse wave transmission time period; and
    a radio frequency (RF) unit for transmitting an analyzed result under the control of the controller,
    wherein at least one of the first electrode, second electrode, and third electrode is configured as a switch to trigger measuring the electrocardiogram signal and the pulse wave signal if one of the first electrode second electrode, and third electrode is touched by user.

2. The mobile terminal of claim 1, wherein the electrocardiogram electrode unit has the third electrode provided on the first side surface of the mobile terminal body adjacent to the second electrode,
    wherein the first, second, and third electrodes represent a positive (+) electrode, negative (−) electrode, and ground electrode, respectively.

3. The mobile terminal of claim 1, further comprising a display unit provided on the front surface of the mobile terminal body adjacent to the first electrode,
    wherein the controller controls the display unit to display the analyzed result.

4. The mobile terminal of claim 1, wherein a portion of the second side surface is substantially planer; and
wherein the optical sensor unit comprises the light source and the light receiver presenting exterior planar surfaces which are substantially flush with attic substantially planar portion of the second side surface.

5. A mobile terminal for measuring biological signals, comprising:
an electrocardiogram electrode unit having:
a first electrode and a second electrode provided on a front surface of a body of the mobile terminal to enable contact by the first electrode with a first finger of a hand and a third electrode provided on a rear surface of the mobile terminal body, wherein said first, second, and third electrodes provides means for measuring an electrocardiogram signal as a first biological signal through the first electrode, the second electrode, and the third electrode, wherein the first and second electrodes are respectively positioned on the front surface near at least one of a first and second side of the mobile terminal body to enable contact by the third electrode and the second electrode with the arm opposite to the hand;
a first optical sensor unit provided on a first side surface and a second optical sensor unit provided on a second side surface of the mobile terminal body, wherein each of the first and second optical sensor units includes a light source for emitting light at tissue, and includes a light receiver for receiving the emitted light reflected by the tissue, with each optical sensor unit optically measuring at least one pulse wave signal and generate at least a second biological signal from the at least one pulse wave signal, wherein the first and second optical sensor units are positioned at the first and second side surfaces of the mobile terminal body, respectively to enable contact by the first optical sensor unit with a second finger of the hand simultaneously with contact by the first electrode with the first finger;
a controller within the mobile terminal for analyzing the electrocardiogram signal received from the electrocardiogram electrode unit and the at least a second biological signal received from the first and second optical sensor units to determine a pulse wave transmission time period; and
an RF unit for transmitting an analyzed result under the control of the controller,
wherein at least one of the first electrode, second electrode, and third electrode is configured as a switch to trigger measuring the electrocardiogram signal and the pulse wave signal if one of the first electrode, second electrode and third electrodes is touched by user.

6. A mobile terminal for measuring biological signals, comprising:
a first optical sensor unit provided on a first side surface of a body of the mobile terminal to enable contact by the first optical unit with a first finger of a hand and a second optical sensor unit provided on a second side surface of the mobile terminal body to enable contact by the second optical sensor unit with an arm opposite to the hand, wherein each of said first and second optical sensor units includes a light source for emitting light at tissue, and includes a light receiver for receiving the emitted light reflected by the tissue, with each optical sensor unit for optically measuring at least one pulse wave signal and for generating at least a first biological signal from the at least one pulse wave signal, wherein the first and second optical sensor units are positioned at the first and second side surfaces of the mobile terminal body, respectively;
an electrocardiogram electrode unit having a first electrode and a second electrode provided in a front surface of the mobile terminal body to enable contact by the first electrode with a second finger of the hand simultaneously with contact by the second optical sensor with the first finger and a third electrode provided in the second side surface of the mobile terminal body adjacent to a corresponding the second optical sensor unit, said electrocardiogram electrode unit measuring an electrocardiogram signal as a second biological signal through the first electrode, the second electrode, and the third electrode, wherein the third electrode is positioned in the one of the first and second side surfaces nearest to the second electrode to enable contact by the second and third electrode with the arm;
a controller for analyzing the electrocardiogram signal received from the electrocardiogram electrode unit and the at least a first biological signal received from the first and second optical sensor units to determine a pulse wave transmission time period; and
an RF unit for transmitting an analyzed result under the control of the controller,
wherein at least one of the first electrode, second electrode, and third electrode is configured as a switch to trigger measuring the electrocardiogram signal and the pulse wave signal if one of the first electrode, second electrode, and the third electrode is touched by user.

7. A mobile terminal for measuring biological signals, comprising:
a first optical sensor unit provided in a first side surface of a body of the mobile terminal to enable contact by the first optical sensor unit with a first finger of a hand and a second optical sensor unit provided in a second side surface of the mobile terminal body to enable contact by the second optical sensor unit with an arm opposite of the hand, wherein each of said first and second optical sensor units includes a light source for emitting light at tissue, and includes a light receiver for receiving the emitted light reflected by the tissue, with each optical sensor unit for optically measuring at least a pulse wave signal and for generating at least a first biological signal from the pulse wave signal, wherein the optical sensors are positioned at the first and second side surfaces of the mobile terminal body, respectively;
an electrocardiogram electrode unit having a first electrode provided in the first side surface to enable simultaneous contact of the first electrode with a second finger of the hand and a second electrode provided in the second side surface of the mobile terminal body adjacent to the sensor units provided therein and a third electrode provided on a front surface of a body of the mobile terminal, to enable contract by the second electrode and the third electrode with the arm, said first, second and third electrodes, in combination, measuring an electrocardiogram signal as a second biological signal, wherein the first and second electrodes are positioned at a lower end of the first and second side surfaces, respectively;
a controller provided for analyzing the electrocardiogram signal received from the electrocardiogram electrode unit and the at least a first biological signal received from the first and second optical sensor units to determine a pulse wave transmission time period; and
an RF unit for transmitting an analyzed result under the control of the controller,
wherein at least one of the first electrode, second electrode, and third electrode is configured as a switch to trigger measuring the electrocardiogram signal and the pulse wave signal if one of the electrodes is touched by user.

* * * * *

UNITED STATES PATENT AND TRADEMARK OFFICE
CERTIFICATE OF CORRECTION

PATENT NO. : 9,326,694 B2
APPLICATION NO. : 12/350282
DATED : May 3, 2016
INVENTOR(S) : Jae Geol Cho et al.

It is certified that error appears in the above-identified patent and that said Letters Patent is hereby corrected as shown below:

In the Claims

Column 8, Claim 1, Line 55 should read as follows:
--...the first electrode, second...--

Column 9, Claim 4, Line 5 should read as follows:
--...flush with a substantially...--

Column 9, Claim 5, Line 50 should read as follows:
--...third electrode is touched...--

Column 10, Claim 7, Line 52 should read as follows:
--...enable contact by the...--

Signed and Sealed this
Twenty-first Day of June, 2016

Michelle K. Lee
*Director of the United States Patent and Trademark Office*